United States Patent [19]

Sagner et al.

[11] Patent Number: 5,714,318
[45] Date of Patent: Feb. 3, 1998

[54] SIMULTANEOUS SEQUENCING OF NUCLEIC ACIDS

[75] Inventors: Gregor Sagner, Penzberg; Christoph Kessler, Dorfen; Helmut Blum, München; Horst Domdey, Neuried, all of Germany

[73] Assignee: Boehringer Mannheim GmbH, Mannheim, Germany

[21] Appl. No.: 182,172

[22] PCT Filed: Jun. 1, 1993

[86] PCT No.: PCT/EP93/01376

§ 371 Date: Feb. 2, 1994

§ 102(e) Date: Feb. 2, 1994

[87] PCT Pub. No.: WO93/24654

PCT Pub. Date: Dec. 9, 1993

[30] Foreign Application Priority Data

Jun. 2, 1992 [DE] Germany .................. 42 18 152.6

[51] Int. Cl.⁶ .................. C12P 19/34; C12Q 1/68; C12N 15/09; C07H 21/04
[52] U.S. Cl. .................. 435/6; 435/91.4; 435/91.41; 435/172.3; 536/24.2
[58] Field of Search .................. 435/6, 172.3, 91.4, 435/91.41; 536/24.2

[56] References Cited

U.S. PATENT DOCUMENTS 4,942,124   7/1990   Church .................. 435/6

FOREIGN PATENT DOCUMENTS

WO 92/22650   12/1992   WIPO .

OTHER PUBLICATIONS

Sambrook et al (1989) In Molecular Cloning: A Laboratory Manual, 2nd ed. Cold Spring Harbor Laboratory Press: Cold Spring Harbor, NY, pp. 8.23–8.25.

New England Biolabs 1992 Catalog, © 1992, p. 158.

Maniatis et al. (1983) In Molecular Cloning: A Laboratory Manual, Cold Spring Harbor Laboratory Press: Cold Spring Harbor, NY 1 page.

Primary Examiner—Jasemine C. Chambers
Assistant Examiner—Scott D. Priebe
Attorney, Agent, or Firm—Nikaido, Marmelstein, Murray & Oram LLP

[57] ABSTRACT

The invention concerns a new method for the simultaneous sequencing of nucleic acids using numerous double-stranded DNA adaptors.

27 Claims, 3 Drawing Sheets

MEANING OF THE SYMBOLS:

PRIMER SITES FOR THE ENZYMATIC SEQUENCING

TRANSCRIPTION TERMINATORS

SPECIAL SEQUENCE CONTAINING NO TARGET SEQUENCES BUT INSTEAD AT LEAST 2 DIFFERENT RESTRICTION SITES WHICH YIELD STEPPED ENDS WHEN CLEAVED WITH THE RESPECTIVE ENZYME

RECOGNITION SITE FOR NotI OR ANOTHER RARELY OCCURRING RESTRICTION ENZYME

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

AATTCCATAA CTGTAACCTT TAAC 24

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:2:

GTTAAAGGTT ACAGTTATGG 20

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

CTATTTGTAA TTCCGCTGCA 20

( 2 ) INFORMATION FOR SEQ ID NO:4:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:4:

GCGGAATTAC AAATAG 16

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:5:

TATATATAGG GTATTAGGTG                                                          20

( 2 ) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

TGAGTATATT GATGATTAGG                                                          20

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

AGAAGTTAAT GTAGGGTTGG                                                          20

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

GTGATAAGTA GAGTTGGTTG                                                          20

( 2 ) INFORMATION FOR SEQ ID NO:9:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

GGCCACATAA CTCAAATCTC AAA                                                      23

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

GGCCAGCTAT CTCGTAATTG CT                                                       22

( 2 ) INFORMATION FOR SEQ ID NO:11:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:11:

GAGTTATGTG GCCGCCACC                                                                    19

( 2 ) INFORMATION FOR SEQ ID NO:12:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:12:

AGACGGCCAC ATAACTCAAA                                                                   20

( 2 ) INFORMATION FOR SEQ ID NO:13:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:13:

CGAGATAGCT GGCCGCCA                                                                     18

( 2 ) INFORMATION FOR SEQ ID NO:14:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:14:

AGAGCGGCCA GCTATCTC                                                                     18

( 2 ) INFORMATION FOR SEQ ID NO:15:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:15:

ATTAACCCTC ACTAAAG                                                                      17

( 2 ) INFORMATION FOR SEQ ID NO:16:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear (i i) MOLECULE TYPE: DNA (x i) SEQUENCE DESCRIPTION: SEQ ID NO:16:

GGCCTTTGAG ATTTGAGTTA TGT            23

(2) INFORMATION FOR SEQ ID NO:17:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (i i) MOLECULE TYPE: DNA (x i) SEQUENCE DESCRIPTION: SEQ ID NO:17:

GGCCAGCAAT TACGAGATAG CT            22

SIMULTANEOUS SEQUENCING OF NUCLEIC ACIDS

This application is a National Stage Application of PCT Application No. PCT/EP93/01376, filed Jun. 1, 1993, which claims priority from German Application No. P 42 18152.6, filed Jun. 2, 1992.

The present invention concerns a new method for the simultaneous sequencing of nucleic acids as well as a method for converting an already existing gene bank into a modified gene bank on which a simultaneous sequencing of nucleic acids can be carried out.

The sequence of nucleic acids is usually determined either by chemical DNA sequencing (Maxam-Gilbert technique) or by the enzymatic chain termination method (Sanger technique). In the Maxam-Gilbert technique a base-specific cleavage of the nucleic acid to be sequenced is carried out with the aid of certain chemicals. In the Sanger technique an enzymatic polymerization reaction is carried out using the nucleic acid to be sequenced as a template and a DNA polymerase, e.g. the Klenow fragment of $E.$ $coli$ DNA polymerase, of T4 DNA polymerase or of T7 DNA polymerase. 2',3'-dideoxynucleoside-5'-triphosphates (ddNTP) are used as a substrate for the enzyme as chain terminating molecules in addition to the normal deoxynucleoside triphosphates (dNTP). Incorporation of these dideoxy compounds into a freshly synthesized DNA strand causes a termination of the polymerization reaction.

The sequence of the individual steps in the procedure is essentially the same in both of the aforementioned techniques: Firstly a high molecular DNA to be sequenced is broken down into several smaller fragments whose sequence can then be determined. This fragmentation can for example be achieved by specific cleavage with restriction enzymes or also by unspecific cleavage with DNase I or by ultrasonic treatment of the DNA.

The actual determination of the sequence is carried out on the smaller fragments, the principle of both sequencing procedures being that a population of sequencing products of different length whose nucleotide sequence derives from that of the DNA to be sequenced is generated by a chemical or enzymatic reaction. One end of these sequencing products is identical for the entire population and the other end is a variable end with one in each case of the four possible bases of DNA. The sequencing products of different length are then separated from one another by separation according to size in general by gel electrophoresis in very thin, high resolution denaturing polyacrylamide gels.

The determination of the sequence is generally carried out by direct analysis of these sequence gels. In this case the sequencing products must have a direct label e.g. by incorporation of radioisotopes such as $^{32}P$ or $^{35}S$ or biotinylated or fluorescent-labelled nucleotides.

The disadvantage of a direct labelling of the sequencing products is that always only one single DNA fragment can be processed in each case in each base-specific sequencing reaction. This disadvantage can be eliminated by a simultaneous sequencing of nucleic acids according to the so-called multiplex technique (see e.g. EP-A 0 303 459). This technique allows the simultaneous processing of several, in general up to 50 different DNA fragments in each base-specific sequencing reaction. For this the DNA fragments to be sequenced are incorporated into different cloning vectors. These vectors differ in each case in that oligonucleotide sequences that are specific for the vector used are located to the left and right of the cloning site. All vectors carry the same cleavage site for a restriction enzyme outside these oligonucleotide sequences with which the cloned DNA fragments together with the neighbouring regions which are specific for them can be again cleaved from the vector. A Maxam-Gilbert sequence reaction is carried out on this fragment mixture. After gel-electrophoretic separation of the sequencing products, the bands are transferred from the sequence gel onto a nylon membrane and are immobilized there. By hybridizing this membrane with hybridization probes that in each case are specific for only one vector it is possible to visualize the sequences of several DNA fragments in succession on the same membrane. The advantage of this method is that the four base-specific sequencing reactions and the separation of the sequencing products which are obtained thereby only have to be carried out once.

However, a disadvantage of this strategy is that numerous vectors each with different specific oligonucleotide sequences are necessary to clone the DNA fragment. A further disadvantage of the multiplex procedure is that the cloning of the DNA into the individual vectors is solely possible by a blunt end ligation. Not only is the cloning efficiency comparably low in this type of cloning but a certain percentage of the colonies contain pure vector DNA due to the low ligation efficiency. This portion has to be separated by a preparative gel electrophoresis before the sequencing.

As a result of the aforementioned disadvantages the multiplex sequencing strategy only has a relatively limited application. Thus the object of the present invention was to develop a method for the simultaneous sequencing of nucleic acids in which the aforementioned disadvantages, in particular the use of numerous base vectors and the low cloning efficiency is eliminated.

Figure 1:
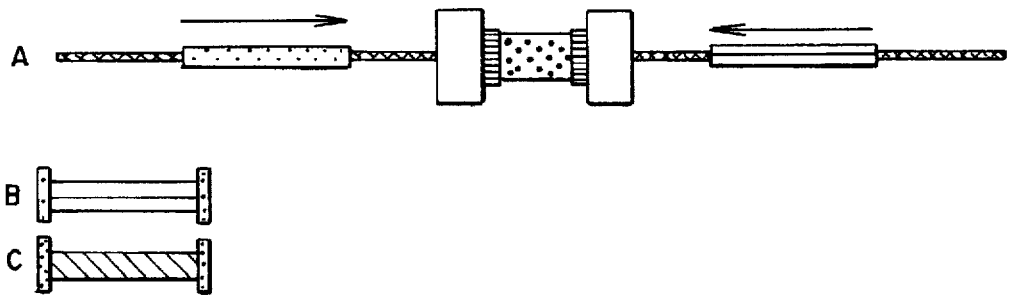
FIG. 1 shows the components required as starting materials for a preferred embodiment of the method according to the invention, a vector (A) and two adaptor molecules (B) and (C).
Figure 1:
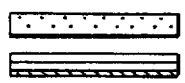
Figure 1:
Figure 1:
Figure 1:

The object according to the invention is achieved by a method for the simultaneous sequencing of nucleic acids which is characterized by (a) provision of numerous DNA fragments whose sequence is to be determined, (b) division of the totality of the DNA fragments to be sequenced into several groups, (c) ligation of double-stranded DNA adaptors to both ends of the divided DNA fragments from (b) wherein the adaptors have a double-stranded region with a length of $\geq 5$ nucleotides, have a first end that is compatible to the ends of the DNA fragments and a second end suitable for cloning into a vector and wherein adaptors having a different nucleotide sequence are ligated to each group of the divided DNA fragments, (d) cloning the DNA fragments from (c) that are provided at both ends with adaptors into a base vector which has restriction sites matching the second ends of the adaptors, (e) selection of a number of clones from (d), in which however, only 1 clone at most may originate from one group and carrying out sequencing reactions on the selected clones and (f) analysis of the results of the sequencing reactions using a number of detectable hybridization probes each of which are specific for only one single clone from (e).

The advantages of the method according to the invention compared to the known multiplex method are in particular that, in contrast to the known multiplex system, only a single base vector is required. As a consequence the adaptor sequences which in the last reaction step determine the binding of the hybridization probe used in each case to the immobilized nucleic acid, can already be ligated to the DNA fragments to be sequenced outside the vector. Thus the totality of the DNA fragments to be sequenced can be divided into any desired number of groups since the number of these groups is not limited by the number of available vectors. The required different adaptor oligonucleotides which are preferably 10 to 40 nucleotides long can be chemically synthesized in a simple manner with any desired sequences. The efficiency of the ligation of the DNA fragments with the adaptor molecules can be considerably improved by using an excess of adaptor molecules. This also results in higher yields of colonies obtained per DNA used in comparison to the known multiplex system.

The DNA fragments provided according to step (a) of the method according to the invention can have blunt or stepped ends. DNA fragments with blunt ends can for example be obtained by cleaving the DNA and if necessary subsequent polishing of the ends in any desired manner. These DNA fragments are preferably produced by disintegrating DNA by means of ultrasound and enzymatic treatment (e.g. with T4 DNA polymerase or Klenow polymerase) of the ends, cleavage with blunt-cutting restriction enzymes, mechanical shearing of DNA or/and by DNase treatment. DNA fragments with stepped ends are preferably produced by cleaving DNA with appropriate restriction enzymes or/and other sequence-specific cutting enzymes.

Step (b) of the method according to the invention comprises dividing the totality of the DNA fragments to be sequenced into several groups. There can be any desired number of these groups and it depends for example on the size of the total DNA to be sequenced. For example the DNA fragments to be sequenced can be divided into 10 to 1000, preferably 50 to 500 groups or fractions.

These individual groups of DNA fragments are ligated according to step (c) of the method according to the invention to double-stranded DNA adaptors which on one side have a first end that is compatible to the DNA fragments. This end can be blunt or stepped as set forth above. The adaptors have a second end on their other side which is suitable for cloning into a vector. This end can be blunt but it is preferably stepped since in this case the cloning of the DNA fragments to be sequenced into the base vector is not carried out via a blunt end ligation but rather via a ligation of DNA fragments with stepped ends so that a substantially improved cloning efficiency is found.

It is expedient that the length of the double-stranded region of an adaptor is sufficient to enable a ligation of the adaptor to the DNA fragment. In general the double-stranded region must therefore be ≧5 nucleotides, preferably ≧6 nucleotides long.

Adaptors of a different nucleotide sequence are ligated to each group of the divided DNA fragments. In this process within one group one can either use a single adaptor or even a mixture of two adaptors which differ in their nucleotide sequence or/and in their second end (intended for cloning into the vector). In this connection the term "different nucleotide sequence" means that the nucleotide sequence of adaptors from different groups (or even within a group) differs to the extent that no cross-hybridization takes place during the analysis of the sequencing reaction using different labelled hybridization probes in step (f) of the method according to the invention. Further criteria which should preferably be observed when selecting adaptor sequences are a melting point that should be as high as possible (GC content), the absence of internal hairpin structures and the presence of "rare" sequences which only occur with a low probability in the DNA fragments to be sequenced (e.g. 5'-CG-3' in eukaryotic DNA). In addition it is preferred that the adaptor sequences used have a melting point which is as uniform as possible so that the sequencing can be more readily automated.

For the ligation reaction within each group one can use a single adaptor or two adaptors with a different nucleotide sequence or/and different second ends, the latter possibility being preferred. If different adaptors are used with different second ends it is therefore necessary to use a base vector for the cloning of the DNA fragments provided with adaptors which has been opened at two different restriction sites matching the respective ends of the adaptors, i.e. has been unsymmetrically hydrolysed. The restriction sites for cloning the DNA fragment are arbitrary provided that when they are cleaved with the respective enzyme they yield matching (and preferably non-compatible) ends. Examples of this are EcoRI, PstI, HindIII sites etc. In addition it is of course expedient that the restriction sites used for the cloning are singular sites on the base vector.

The base vector preferably has at least one so-called "rarely occurring" enzymatic cleavage site on both sides of the insertion site. A rarely occurring cleavage site is understood as a cleavage site, which due to its specific characteristics, is expected to occur within the DNA to be sequenced only with a very low probability. Examples for such cleavage sites are for instance restriction sites with a recognition sequence of at least 7 nucleotides (e.g. NotI, SfiI, RsrII, SgrAI, SwaI, PacI, AscI, PmeI, Sse8387I, SrsI or I-SceI sites) or/and those restriction sites which contain the nucleotide sequence 5'-CG-3' at least once within their recognition sequence which occurs extremely rarely in eukaryotic DNA. This rarely occurring cleavage site can be used to cut out the cloned DNA from the vector without a cleavage within the DNA.

In addition it is preferred but not necessary to use a base vector for the cloning of the DNA fragments provided with adaptors which has transcription terminators in the vicinity of the restriction sites used for the insertion of the DNA fragments so that no negative interactions of the vector with the host cell due to a possible transcription of the cloned DNA sequences can occur. Preferred examples of suitable base vectors are for instance those which have a "multiple cloning site" with corresponding suitable singular restriction sites for cloning. Examples of this are in particular the commercially available dideoxy sequencing vectors which are set forth in Table 7.1.1 of Ausubel et al., Current Protocols in Molecular Biology, Supplement 16 (chapter 7.1.3). From these statements it is clear that the requirements for the usability of a vector for the method according to the invention are much less than for the usability of a vector in the known multiplex method.

Step (e) of the method according to the invention comprises the selection of a number of different clones from (d), in which, however, only one clone at most may originate from a particular group, and carrying out sequencing reactions on these selected clones. The preparation of these clones can for example be achieved by a transformation of the ligated DNA into suitable host cells (preferably *E. coli* cells) after the cloning step according to (d), an amplification of the gene bank obtained in this manner and an examination of individual clones from this gene bank for the presence of an inserted DNA vector according to known methods (e.g. preparative gel electrophoresis and isolation of plasmid DNA).

The sequencing reaction on the selected clones is in principle carried out as in the already known multiplex sequencing method either by a chemical method or by an enzymatic chain termination method. In this process the individual base-specific reactions (either according to the Sanger technique or according to the Maxam-Gilbert technique) are preferably carried out directly on the mixture of different DNA fragments i.e. simultaneously.

In a chemical method according to Maxam-Gilbert, the DNA fragments to be sequenced including the adaptors must firstly be cut out from the vector. This can for example be accomplished at the restriction sites at which the cloning into the vector has also taken place. In this manner the DNA fragments cloned in step (d) are released again. However, "rarely occurring" cleavage sites are preferably used for this purpose which are in the vicinity of the cloning site, preferably at a distance of less than 100 nucleotides. By this means the probability of a cleavage within the DNA to be sequenced is extremely low. The cut out fragments are subsequently purified of vector DNA. This is preferably achieved by preparative Agarose gel electrophoresis. In this way one obtains a mixture of DNA fragments in which each DNA fragment has adaptor molecules in the region of its two ends that are different from the adaptor molecules of another DNA fragment. This mixture is subsequently treated according to a known Maxam-Gilbert protocol. This generally involves a division of the mixture into four aliquots in which each aliquot is treated with a different, base-specific chemical reagent that finally leads to a statistical cleavage of the DNA fragments at the respective bases. Consequently a population of sequencing products is produced whose sequence can be determined in a next step.

In an enzymatic chain termination method according to Sanger it is not necessary to cut out the DNA fragments from the vector. The mixture of vectors with different cloned DNA fragments is firstly denatured. A primer oligonucleotide that is complementary with a region of the vector in the vicinity of the cloned DNA fragment or/and with the adaptor and therefore binds to the denatured DNA is added to the resulting single-stranded DNA. If it is intended to carry out the sequencing of the DNA fragment from two sides then two different primer molecules can be added to each preparation. After dividing the mixture obtained in this way into four aliquots a polymerisation reaction with a DNA polymerase is carried out according to the known Sanger protocol in each case in the presence of a different chain terminating molecule. The population of sequencing products produced in this manner is subsequently treated further as described in the following.

Step (f) of the method according to the invention, the analysis of the sequencing reaction using detectable hybridization probes that in each case are specific only for one single clone from the total number of clones comprises generally the following steps:

(f1) separating the sequencing products obtained by the sequencing reactions from (e) according to their size in which corresponding sequencing products of a particular reaction from several clones are separated together, (f2) transferring the separated sequencing products onto a suitable carrier for binding nucleic acids and if desired, immobilization of the transferred sequencing products on the carrier, (f3) reversible hybridization of the carrier with (i) a first detectable hybridization probe or (ii) with two or several selectively detectable hybridization probes in which each probe is in each case only specific for a single clone from (e) and in which the specificity of each probe is defined by a hybridization to a particular target sequence carried out under the reaction conditions, which is formed from a particular adaptor and if desired neighbouring vector sequences, (f4) analysis of the results from (f3), removal of the bound hybridization probes from the carrier and (f5) if desired, repetition of steps (f3) and (f4) with further detectable hybridization probes which differ from the other probes in that they bind to other target sequences.

The separation of the sequencing products (f1) is preferably carried out by gel electrophoresis, particularly preferably by a denaturing polyacrylamide gel electrophoresis in a special sequence gel. A membrane made of nitrocellulose, nylon, polyvinylidene fluoride or chemically activated cellulose (e.g. diazocellulose) is preferably used as the carrier onto which the separated sequencing products are transferred (f2). The transfer of the DNA fragments onto the carrier and their immobilization is carried out with the aid of known blotting techniques (see e.g. Sambrook et al., A Laboratory Manual, Cold Spring Harbor Laboratory Press, 1989).

This is followed by a reversible hybridization of the carrier with a first detectable hybridization probe which in each case is only specific for a single clone. It is, however, also possible to use two or more hybridization probes simultaneously provided that due to different labels they can be selectively detected concurrently. The specificity of a probe is determined in this case solely by the group-specific or clone-specific adaptor. When using shorter adaptors, the hybridization of the probe can take place not only at the adaptor itself but also additionally at neighbouring vector sequences. The length of the hybridization region between the probe and the specific target sequence is preferably 10 to 50 nucleotides, particularly preferably 15 to 40 nucleotides. In this manner a hybridization is achieved that enables the determination of the nucleic acid sequence.

The removal of a probe hybridizing reversibly to the complementary target sequence from the carrier is also carried out according to known methods e.g. by heating above the melting point of the hybrid in the presence of SDS (see e.g. Sambrook et al., supra).

Radioactively-labelled as well as non-radioactively-labelled hybridization probes can be used for the method according to the invention. It is preferable to use non-radioactively-labelled probes such as biotin, fluorescent, luminescent, digoxigenin or/and enzyme (e.g. peroxidase or alkaline phosphatase) labelled probes. It is particularly preferable to use probes that are labelled with digoxigenin or derivatives thereof. Probes according to the invention can be produced in a simple manner by chemical synthesis in which the incorporation of labelled nucleotides can be achieved during the synthesis. On the other hand the probe can also be radioactively labelled subsequently e.g. by 5'-phosphorylation.

In the attached drawing a particularly preferred embodiment of the method according to the invention for simultaneous sequencing is again shown schematically. The components required as starting material are a vector (A) and two adaptor molecules (B) and (C) which are composed of double-stranded DNA and each of which are provided on one side with a blunt end and on the other side with a protruding end.

FIG. 1 shows the starting materials.

The vector is hydrolysed with two different restriction enzymes each of which produce protruding, non-compatible ends.

Figure 2:
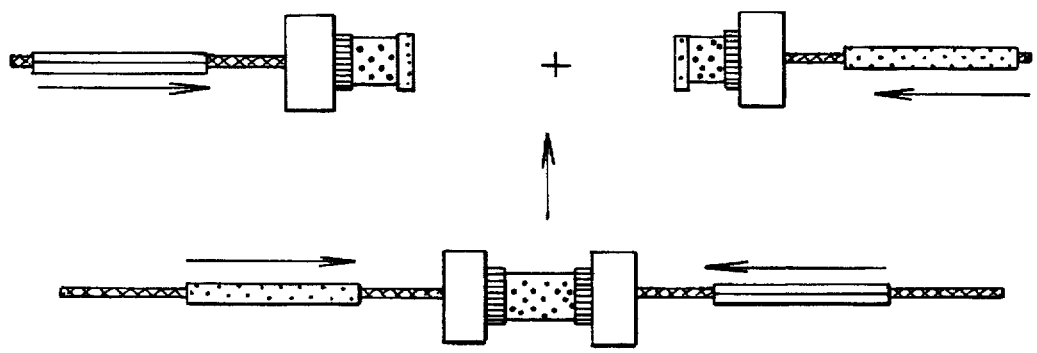
FIG. 2 shows the hydrolysis of the vector (A) with restriction enzymes.

FIG. 2 shows this hydrolysis.

The sequencing DNA with blunt ends (D) is ligated to the adaptor molecules and cloned into the opened vector. For this the sequencing DNA obtained is preferably separated by Agarose gel electrophoresis and a region of a desired size, preferably 800 bp to 1200 bp is cut out from the gel and eluted.

Figure 3:
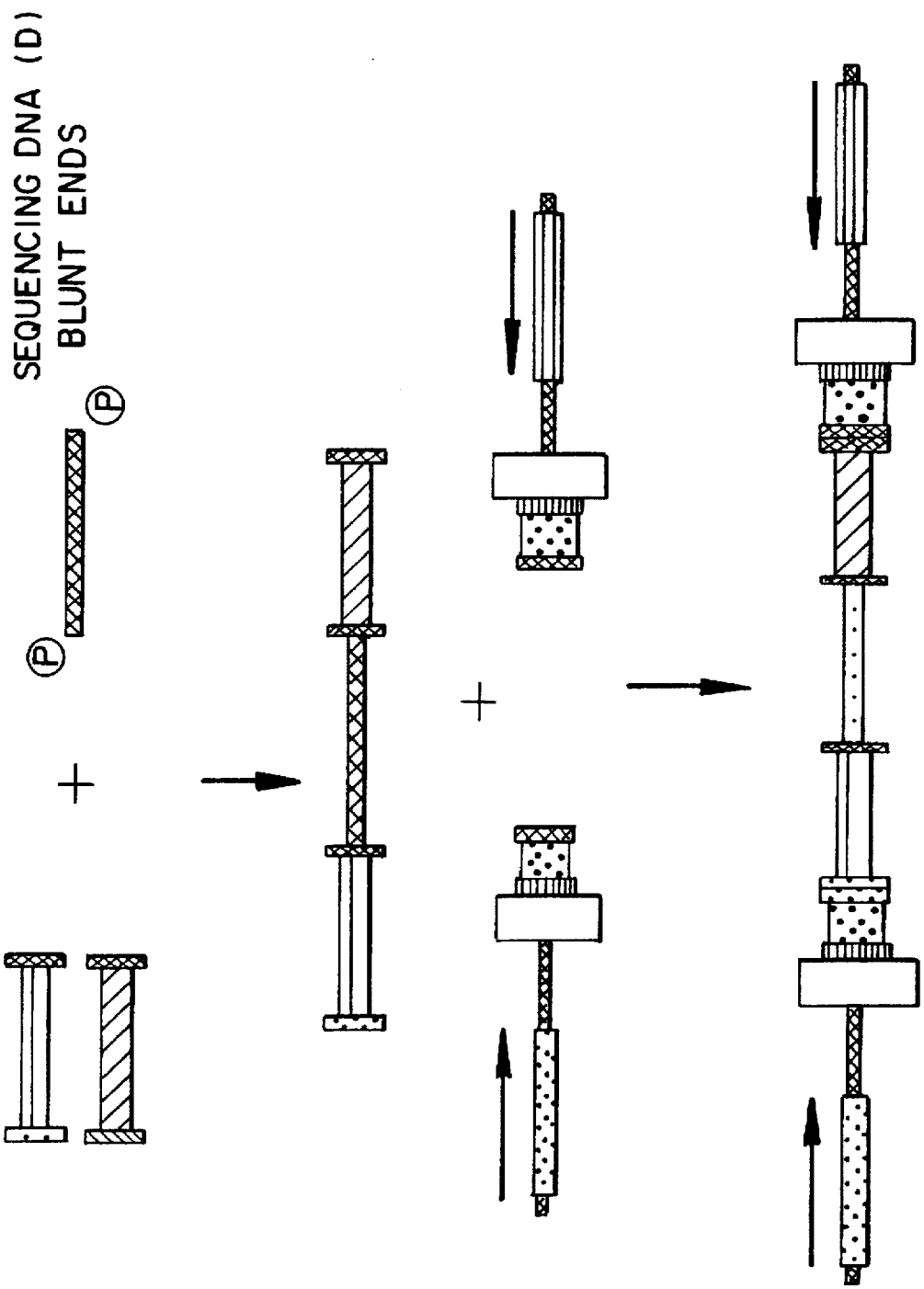
FIG. 3 illustrates the ligation of sequencing DNA (D) to the adaptor molecules (B) and (C), and the cloning of this complex into the opened vector (A).

FIG. 3 illustrates this schematically.

The vector obtained in this way with inserted DNA can be proliferated by transformation into suitable cells (in general *E. coli* cells) and isolated.

The present invention in addition concerns a method for converting an already existing gene bank into a modified gene bank on which a simultaneous sequencing of nucleic acids (as described above) can be carried out. The term "gene bank" means in this case that a number of different DNA fragments (to be sequenced) are present as insertions in a base vector. The method for modifying a gene bank is based on the introduction of a double-stranded DNA adaptor molecule into the vector in the vicinity of the insertions to be determined by which means when several different adaptor molecules are used it is possible to divide the gene bank into a number of groups on which a simultaneous sequencing can be carried out.

This method comprises the steps:

(a) providing any desired gene bank consisting of a multitude of different DNA fragments which have been cloned into a base vector in which the base vector contains at least one singular, rarely occurring enzymatic cleavage site in the vicinity of the cloned DNA fragments, (b) linearizing the gene bank by cleavage at a rarely occurring cleavage site according to (a), (c) dividing the gene bank into several groups, (d) ligating the divided, linearized gene bank with a double-stranded DNA adaptor, the double-stranded region of the adaptor having a length of $\geq 5$ nucleotides and ends on both sides which match the cleavage site of the base vector, whereby an adaptor with a different sequence is ligated to each group of the gene bank and (e) if desired, separating the desired ligation products from by-products.

In this process the nucleotide sequence of the adaptor molecule is preferably selected so that the cleavage site in the vector is eliminated by introduction of the adaptor. This enables the desired ligation products to be separated from by-products by recleaving them with the restriction enzyme used in step (b) for linearizing the gene bank. In this manner a religated vector (without adaptor molecule insertion) is opened again so that the vector with cloned DNA is obtained as the only transformable product. The "rarely occurring cleavage site" in this method is as defined above i.e. it preferably has a recognition sequence of at least 8 nucleotides length or/and has at least once the nucleotide sequence 5'-CG-3', e.g. a NotI, SfiI, RsrII, SgrAI, SwaI, PacI, AscI, PmeI, Sse8387I, SrsI or I-SceI recognition site.

A particularly preferred embodiment for converting conventional gene banks into gene banks on which a simultaneous DNA sequencing is possible is described schematically in the following. In this process one starts with a gene bank in a base vector (A) which has a rarely occurring restriction site (e.g. NotI) in the vicinity of the insertion. Modern high performance vectors (e.g. pBsSk vectors) are preferably used as base vectors. Furthermore one requires a set of special adaptor oligonucleotides (B) as starting material which have compatible ends for the restriction site. The adaptor molecules are preferably dephosphorylated and the sequences next to the protruding regions at the end should preferably not correspond to the NotI recognition sequence. The double-stranded region of the adaptor molecule contains the target sequences required for the simultaneous DNA sequencing (to which the hybridization probe is later to bind). Therefore a correspondingly high number of adaptor molecules with "different nucleotide sequence" (see above definition) is required. In particular no cross-hybridization should occur between the individual adaptor molecules which would interfere with the sequence determination.

In a first step the vector is hydrolysed at a rarely occurring restriction site (in this case NotI) in the vicinity (preferably $\leq 100$ nucleotide distance) of the DNA insertion and divided into several groups. Subsequently each group of the hydrolysed vector is ligated with a different, the double-stranded adaptor molecule.

Figure 4:
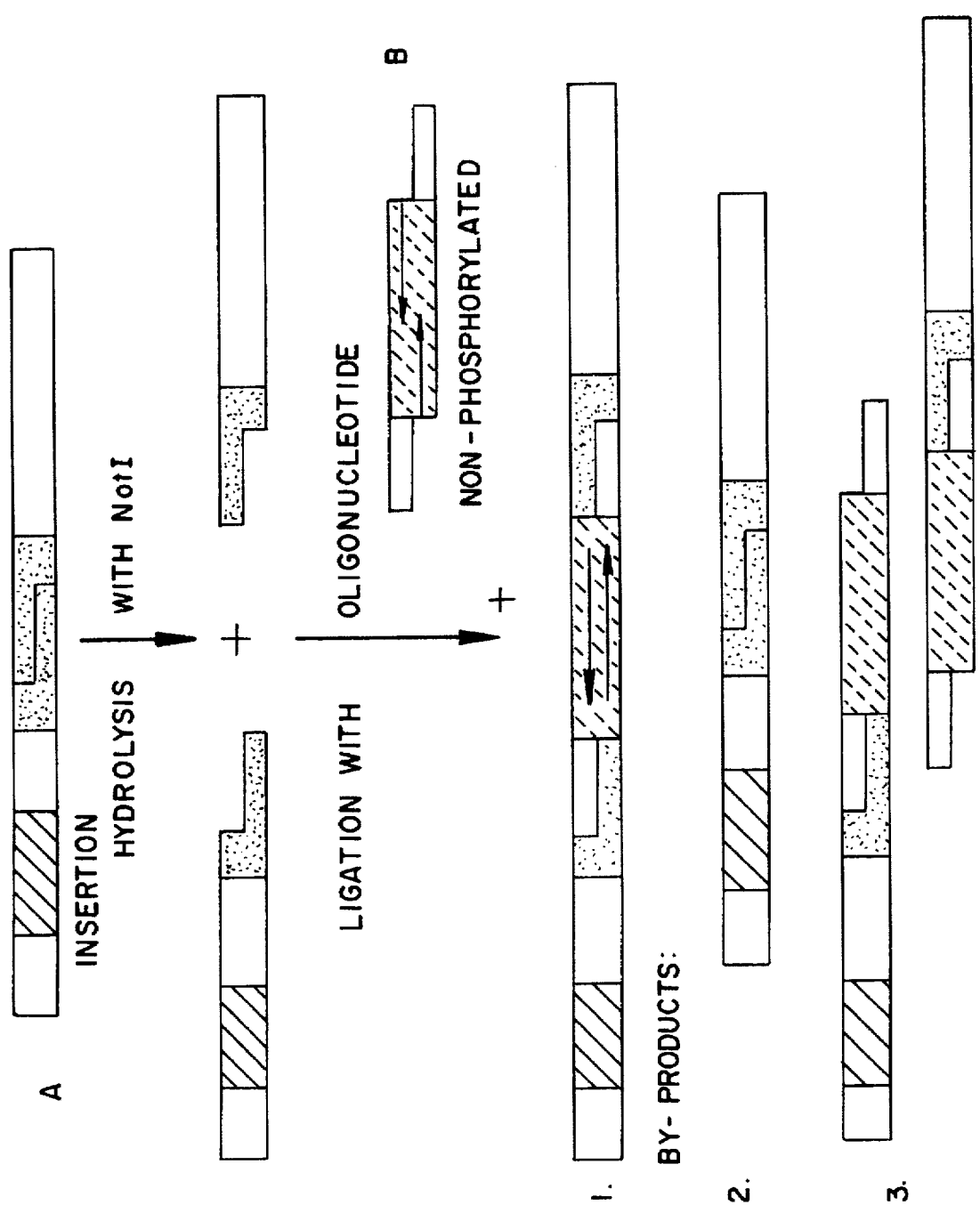
FIG. 4 shows schematically a particularly preferred embodiment for converting conventional gene banks into gene banks on which a simultaneous DNA sequencing is possible.

In this process undesired by-products (2) and (3) are formed in addition to the desired product (1) of which (3) is non-transformable (and therefore does not require a special separation) and (2) can be again linearized by recleaving with NotI and thus made untransformable (when the nucleotide sequence of the adaptor molecule is selected so that the NotI site is removed). This is shown schematically in FIG. 4.

The sequencing reaction on such a gene bank is carried out according to the principle which has already been described above.

In the modification of a gene bank according to the invention one can on the one hand use a double-stranded adaptor molecule which has a symmetrical sequence and is composed of two identical self-complementary oligonucleotides, but on the other also use an adaptor molecule which has an unsymmetrical sequence. The use of an unsymmetrical adaptor molecule is preferred. In this case a mixture of two hybridization probes (each of which is complementary to one strand of the adaptor molecule but are not self-complementary) must be used for the analysis of a sequence reaction.

If a gene bank in a base vector is used as the starting product for the method which contains at least one singular, rarely occurring restriction site on each of the two sides in the vicinity of the cloned DNA fragments to be sequenced, then steps (b) to (e) of the method according to the invention can be carried out twice. In this way there is then a specific adaptor molecule located on both sides of the cloned DNA fragment, each of which can bind a specific hybridization probe in a simultaneous sequencing process as described above so that a sequencing of the cloned DNA fragment starting at both ends of the fragment is possible.

It is in addition intended to elucidate the invention by the following sequence protocols and examples.

SEQ ID NO: 1 Adaptor (1)

SEQ ID NO: 2 Adaptor (2) In the sequence protocol the complementary strand in the 5'-3' direction of the adaptor used is shown.

SEQ ID NO: 3 Adaptor (3)

SEQ ID NO: 4 Adaptor (4) In the sequence protocol the complementary strand in the 5'-3' direction of the adaptor used is shown.

SEQ ID NO: 5 Multiplex vector 10—Plex 10E

SEQ ID NO: 6 Multiplex vector 10—Plex 10P

SEQ ID NO: 7 Multiplex vector 19—Plex 19E

SEQ ID NO: 8 Multiplex vector 19—Plex 19P

SEQ ID NO: 9 Adaptor GB1. The adaptor DNA is composed in the 5'-3' direction of the bases 1–23 and in the 3'-5' direction of the bases complementary to 5-27.

SEQ ID NO: 10 Adaptor GB2. The adaptor DNA is composed in the 5'-3' direction of the bases 1-22 and in the 3'-5' direction of the bases complementary to 5-26.
SEQ ID NO: 11 Oligonucleotide BG1A
SEQ ID NO: 12 Oligonucleotide BG1B
SEQ ID NO: 13 Oligonucleotide BG2A
SEQ ID NO: 14 Oligonucleotide BG2B
SEQ ID NO: 15 T3 sequencing primer

EXAMPLES

Example 1

Constructing a gene bank according to the multiplex procedure
Fragmentation of the DNA:

10 μg chromosomal yeast-DNA (dissolved in 50 μl 50 mmol/l Tris HCl, 10 mmol/l MgCl$_2$, 10 mmol/l DTT pH 7.8) was sonified in an ultrasonic bath (Sonorex RK255H, BANDELIN, frequency: 35 kHz; power: 160/320 W) until the fragments obtained were smaller than 5 kbp on analysis by means of Agarose gel electrophoresis.
Polishing the ends and separation according to size:

In order to polish the ends, the DNA fragments were reacted for 30 minutes in a volume of 40 μl with Klenow polymerase (0.25 U/μl) and T4 DNA polymerase (0.15 U/μl) in the presence of dNTPs (0.025 mmol/l). After inactivation of these enzymes (10 min. heating at 70° C.), a portion of this DNA was applied to an Agarose gel (0.8% low melting point Agarose, 1×TBE) and separated by electrophoresis (1 h at 4 V/cm).
Isolation of the ca. 1 kbp long fragments:

The region of the gel which contains fragments between 0.5 and 1.1 kbp length was cut out from the gel. The DNA fragments were eluted by freezing the Agarose and subsequent centrifugation and precipitated by addition of 1/10 volumes sodium acetate (3 mol/l, pH 7) and 0.8 volumes isopropanol. The precipitated DNA was washed with 70% EtOH (v/v), dried and taken up in TE (10 mmol/l Tris-HCl, 0.1 mmol/l EDTA pH 8).
Cloning of the fragments in the multiplex vector 10 or 19

About 20 ng of the fragments obtained was ligated with the aid of T4 DNA ligase (0.3 Weiss units/μl) in a volume of 20 μl (50 mmol/l Tris-HCl, 10 mmol/l MgCl$_2$, 10 mmol/l DTT, pH 7.8, 0.5 mmol/l rATP) with 20 ng of the multiplex vector 10 or 19 (corresponding to vectors 1 or 3 of the multiplex kit from the Millipore Co.) (22 h at 16° C.). The multiplex vector was previously hydrolysed under standard conditions with SmaI and subsequently dephosphorylated.
Transformation and culture of DH5a cells Competent DH5α cells obtained commercially were transformed with a tenth of the ligation mixture according to the instructions of the BRL Company and cultured while selecting for tetracycline. 5×10$^5$ independent colonies were obtained per μg DNA in relation to the vector used.
Constructing gene banks which contain exclusively plasmids with cloned yeast DNA A LB plate with about 1000 of the colonies obtained is cultured at 37° C. until the colonies have reached a diameter of ca. 1 to 2 mm. Then the colonies are suspended in LB medium with the aid of a glass spatula, removed from the plate and cultured in a volume of 3 ml while selecting for tetracycline for a further 2 hours. Afterwards the bacteria are sedimented by centrifugation. The plasmid DNA is isolated by alkaline lysis of the cells under standard conditions and purified by column chromatography (Qiagen, minipreparation). A portion of this DNA (ca. 2 μg) is applied to an Agarose gel (0.8% low melting point Agarose, 1×TBE, 0.5 mg/ml ethidium bromide) and separated by electrophoresis (1 h at 4 V/cm). The region of the gel between the "supercoiled form" and the "relaxed form" of the multiplex vector 10 or 19 contains the plasmid DNA with cloned yeast DNA. This region of the gel is cut out. The DNA contained therein is eluted by freezing the Agarose and subsequent centrifugation and precipitated by addition of 1/10 volumes sodium acetate (3 mol/l, pH 7) and 0.8 volumes isopropanol. The precipitated DNA is washed with 70% EtOH (v/v), dried and taken up in TE (10 mmol/l Tris-HCl, 0.1 mmol/l EDTA, pH 8). Competent DH5α cells are transformed with a portion of the DNA obtained and cultured on LB plates while selecting for tetracycline.

Example 2

Constructing a gene bank according to the described method

Chromosomal DNA of yeast was disintegrated into fragments which are smaller than 5 kbp as described in example 1 by sonication with ultrasound. The ends of these DNA fragments were polished by treatment with Klenow polymerase and T4 DNA polymerase. After inactivation of these enzymes (10 min. at 70° C.), 2 μg of this DNA was reacted in a volume of 20 μl (50 mmol/l Tris-HCl, 10 mmol/l MgCl$_2$, 10 mmol/l DTT pH 7.8, 1 mmol/l rATP) with T4 DNA ligase (50 Weiss units per ml) and 2 μg of each of the following adaptor molecules:
Adaptors

| | |
|---|---|
| (1):5'-AATTCCATAACTGTAACC-TTTAAC-3' EcoN(24-mer) | SEQ ID NO:1 |
| (2): 3'-GGTATTGACATTGGAAA-TTG-5' EcoH(20-mer) | SEQ ID NO:2 |
| (3): 5'-CTATTTGTAATTCCGCTG-CA-3' PstH(20-mer) | SEQ ID NO:3 |
| (4): 3'-GATAAACATTAAGGCG-5' PstN(16-mer) | SEQ ID NO:4 |

The processing of the DNA fragments obtained in this way is carried out as described in example 1: After the ligation the DNA fragments were applied to a 0.8% Agarose gel and separated. The fragments which were between 0.5 and 1.1 kbp long were eluted and purified. Afterwards they were cloned into the multiplex vector 10 or 19 which in contrast to example 1 had stepped non-mutually compatible ends by previous treatment with EcoRI and PstI. Competent DH5α cells were transformed with the ligation mixture and cultured on LB plates while selecting for tetracycline.

3×10$^6$ independent colonies per μg DNA were obtained relative to the vector used and thus about 6 times more colonies than in example 1.

Gene banks which contained exclusively plasmids with cloned yeast DNA were constructed as described in example 1.

Example 3

Simultaneous sequencing of gene banks which were constructed according to the multiplex procedure or according to the new procedure.

Single colonies were set up by streaking gene banks which were obtained according to example 1 and example 2. 1 colony from each of the two gene banks were combined in 10 ml LB medium and suspended. The medium was shaken at 37° C. until the suspension had an optical density of 2 at a wavelength of 600 nm. Afterwards the bacteria were sedimented by centrifugation. The plasmid DNA was isolated by alkaline lysis of the cells under standard conditions and purified by column chromatography (Qiagen, minipreparations).

The mixture of the two plasmid DNAs (8 μg) was sequenced using a modified T7 polymerase (sequenase) and the protocols of the USB Co. A mixture of the oligonucleotides Plex E and Plex P (in each case 40 ng per mixture) was used as the sequencing primer which was used as a standard for sequencing according to the multiplex procedure. The sequencing products obtained were separated on a sequence gel (40 cm long, 0.4 mm thick, 6% polyacrylamide, 7 mol/l urea; buffer: 1×TBE), transferred onto a neutral nylon membrane by a capillary blot and immobilized on the membrane by irradiating with 256 nm UV light. The sequence products were detected by hybridization with digoxigenin-treated oligonucleotides which had been obtained by reacting the unmodified oligonucleotides with terminal deoxynucleotidyl transferase and digoxigenin-treated dUTP (Boehringer Mannheim). The corresponding sequence ladders were made visible with the aid of the digoxigenin detection system of the Boehringer Mannheim Company (Fab fragments of anti-digoxigenin antibodies) and subsequent chemiluminescence. After the detection of a sequence reaction, the hybridized oligonucleotide was removed by heating the membrane under standard conditions. The membrane was in each case reacted once with one of the following digoxigenin-treated oligonucleotides:

Multiplex vector 10

| | |
|---|---|
| Plex 10E (5'-TATATATAGGGTATTAGGTG 3') | SEQ ID NO: 5 |
| Plex 10P (5'-TGAGTATATTGATGATTAGG 3') | SEQ ID NO: 6 |

Multiplex vector 19

| | |
|---|---|
| Plex 19E (5'-AGAAGTTAATGTAGGGTTGG3') | SEQ ID NO: 7 |
| Plex 19P (5'-GTGATAAGTAGAGTTGGTTG-3'), | SEQ ID NO: 8 |

PstH, EcoH (see example 2).
Result:
In each of the hybridizations carried out, an independent unequivocal sequence could be determined.

Example 4

Conversion of an already existing gene bank into a gene bank which is suitable for simultaneous sequencing.
Isolation of the plasmids containing cDNA:

A cDNA bank from human heart set up in the EcoRI cleavage site of the phage vector lambda ZAP II and commercially available from the Stratagene Co. (San Diego, U.S.A.) (Catalogue No. 936208) was firstly converted into the double-stranded phagemid form according to the instructions of the manufacturer.

Hydrolysis with NotI and attachment of the adaptors:

1 µg of the total DNA isolated from the phagemid bank was cleaved under standard conditions with the enzyme NotI. In two separated reactions, 300 ng of the adaptor DNA (mixture 1: adaptor GB1; mixture 2: adaptor GB2) was added in each case to 500 ng of the cleaved DNA. The adaptors were ligated with the DNA (10 h; 12° C.) by reaction with T4 DNA ligase (50 Weiss units/ml) in a volume of 20 µl (50 mM Tris-HCl, 10 mM MgCl$_2$, 10 mM DTT, pH 7.8, 1 mM ATP). The adaptors used have the following sequence:

GB1:

| | |
|---|---|
| 5'-GGCCACATAACTCAAATCTCAAA-3' | SEQ ID NO: 9 |
| 3'-TGTATTGAGTTTAGAGTTTCCGG-5' | SEQ ID NO: 16 |

GB2:

| | |
|---|---|
| 5'-GGCCAGCTATCTCGTAATTGCT-3' | SEQ ID NO: 10 |
| 3'-TCGATAGAGCATTAACGACCGG-5' | SEQ ID NO: 17 |

Separation of the excess adaptors

After the ligation the reaction mixture is heated for 10 minutes to 65° C. and subsequently cooled on ice. The reaction mixtures are applied to an Agarose gel (0.8% low melting point Agarose, 1×TBE, 0.5 mg/ml ethidium bromide) and separated by electrophoresis (1 h at 4 V/cm). The region of the gel containing plasmid DNA (larger than linearized pBsSKII DNA) is cut out. The DNA contained therein is eluted by freezing the Agarose and subsequent centrifugation and precipitated by addition of 1/10 volumes sodium acetate (3 mol/l, pH 7) and 0.8 volumes isopropanol. The precipitated DNA is washed with 70% EtOH (v/v), dried and taken up in TE (10 mmol/l Tris-HCl, 0.1 mmol/l EDTA, pH 8).

Circularization of the plasmid DNA with adaptors at both ends by annealing the cohesive ends.

Ca. 50 ng of the isolated DNA is firstly stored for 20 minutes at 65° C. and then for a further 2 h at 37° C. in a volume of 20 µl (50 mM Tris-HCl, 10 mM MgCl$_2$, 10 mM DTT, pH 7.8).

Construction of gene banks

Competent DH5α cells obtained commercially were transformed with a tenth of the ligation mixtures according to the instructions of the BRL Co. The bacteria are streaked out on LB plates and cultured while selecting for ampicillin. The gene banks constructed in this manner contained—in relation to the vector used—1 to 6×10$^6$ independent colonies per µg of DNA used.

In each case one colony from each of the two gene banks was removed and cultured together in 10 ml LB medium. Plasmid DNA was isolated as described in example 3 and the mixture of the two plasmid DNAs (8 µg) was sequenced using a modified T7 polymerase (sequenase) and the protocols of the USB Co. The T3 sequencing primer (5'-ATTAACCCTCACTAAAG-3'(SEQ ID NO: 15), in each case 40 ng per mixture) was used as the sequencing primer. The sequence products obtained were separated on a sequence gel (40 cm long, 0.4 mm thick, 6% polyacrylamide, 7 mol/l urea; buffer: 1×TBE), transferred onto a neutral nylon membrane by a capillary blot and immobilized on the membrane by irradiation with 256 nm UV light. The sequence products were detected by hybridization with digoxigenin-treated oligonucleotides which have been obtained by reaction of unmodified oligonucleotides with terminal deoxynucleotidyl transferase and digoxigenin-treated dUTP (Boehringer Mannheim). The corresponding sequence ladders are made visible with the aid of the digoxigenin detection system of the Boehringer Mannheim Co. (Fab fragments of anti-digoxigenin antibodies) and subsequent chemiluminescence. After the detection of a sequence reaction, the hybridized oligonucleotide was removed by heating the membrane under standard conditions.

The membrane is reacted in each case once with a mixture of the oligonucleotides BG1A and BG1B and subsequently with a mixture of the oligonucleotide BG2A and BG2B:

| | |
|---|---|
| BG1A: 5'-GAGTTATGTGGCCGCCACC-3' | (SEQ ID NO: 11) |
| BG1B: 5'-AGACGGCCACATAACTCAAA-3' | (SEQ ID NO: 12) |
| BG2A: 5'-CGAGATAGCTGGCCGCCA-3' | (SEQ ID NO: 13) |
| BG2B: 5'-AGAGCGGCCAGCTATCTC-3' | (SEQ ID NO: 14) |

Result:
In each of the hybridizations carried out it was possible to determine an independent unequivocal sequence.

We claim:

1. A method for the simultaneous sequencing of nucleic acids, comprising:

(a) preparing numerous DNA fragments whose sequences are to be determined;

(b) dividing the DNA fragments to be sequenced into several groups;

(c) ligating double-stranded DNA adaptors to both ends of the divided DNA fragments from step (b) to produce DNA fragment/adaptor complexes, wherein the adaptors have a double-stranded region with a length of at least 5 nucleotides, have a first end that is compatible to the ends of the DNA fragments and a second end suitable for ligating into a vector, and wherein adaptors having different nucleotide sequences are ligated to the DNA fragments of each of the several groups;

(d) ligating DNA fragment/adaptor complexes from each of the several groups from step (c) into a base vector comprising a plurality of cleavage sites for a plurality of restriction endonucleases, which base vector has been cleaved with at least one of the restriction endonucleases, wherein the cleavage produces ends matching with the second end of one of the adaptors;

(e) selecting one vector from each of the several groups produced in step (d) and carrying out sequencing reactions on each of the ligated DNA fragment/adaptor complexes present in the selected vectors to produce sequencing products; and (f) producing nucleotide sequence information by separating the sequencing products of step (e) from one another and thereafter identifying the separated sequencing products by hybridizing the separated sequencing products with at least one hybridization probe which comprises a DNA sequence which is complementary or identical to a 5 nucleotide portion of one adaptor of one single DNA fragment/adaptor complex.

2. The method as claimed in claim 1, wherein the at least one hybridization probe comprises a DNA sequence which is complementary to the DNA adaptor portion of the one single DNA fragment/adaptor complex.

3. The method as claimed in claim 1, wherein the DNA fragments of step (a) have blunt ends.

4. The method as claimed in claim 1, wherein the DNA fragments of step (a) have stepped ends.

5. The method as claimed in claim 1, wherein the second end of the double-stranded DNA adapters is stepped.

6. The method as claimed in claim 1, wherein the length of the double-stranded region of the double-stranded DNA adapters is 10 to 40 nucleotides.

7. The method as claimed in claim 1, wherein the double-stranded DNA adapters ligated to each end of the divided DNA fragments consist of the same nucleotide sequence.

8. The method as claimed in claim 1, wherein the double-stranded DNA adapters ligated to each end of the divided DNA fragments consist of different nucleotide sequences.

9. The method as claimed in claim 8, wherein the second ends of the double-stranded DNA adapters are stepped.

10. The method as claimed in claim 9, wherein the stepped second ends of the double-stranded DNA adapters ligated to each end of the divided DNA fragments are non-complementary.

11. The method as claimed in claim 1, wherein the base vector comprises an insertion region for inserting a DNA fragment/adaptor complex, the insertion region flanked on each side by at least one restriction endonuclease recognition sequence which contains at least one of (1) a sequence of at least 7 nucleotides and (2) a 5'-CG-3' nucleotide sequence.

12. The method as claimed in claim 11, wherein the at least one restriction endonuclease recognition sequence is selected from the group consisting of NotI, SfiI, RsrII, SgrAI, SwaI, PacI, AscI, PmeI, Sse83871, SrsI and I-SceI.

13. The method as claimed in claim 1, wherein each of the plurality of cleavage sites is flanked by transcription terminators.

14. The method as claimed in claim 1, wherein the at least one hybridization probes is non-radioactively labelled.

15. The method as claimed in claim 14, wherein the at least one hybridization probe is non-radioactively labelled with a label independently selected from the group consisting of biotin, digoxigenin, a fluorescent label, a luminescent label, and an enzyme.

16. The method as claimed in claim 1, wherein step (f) comprises the following steps:

(f1) separating the sequencing products of step (e) according to the size thereof;

(f2) transferring the separated sequencing products from step (f1) onto a suitable carrier for binding nucleic acids;

(f3) reversibly hybridizing the separated sequencing products from step (f2) with at least one hybridization probe which comprises a DNA sequence which is complementary to one single DNA fragment/adaptor complex; and (f4) producing nucleotide sequence information by analyzing the hybridization of the separated sequencing products from step (f3).

17. The method as claimed in claim 16, wherein the at least one hybridization probe comprises a DNA sequence which is complementary to the DNA adaptor portion of the one single DNA fragment/adaptor complex.

18. The method as claimed in claim 16, wherein step (f2) further comprises immobilizing the transferred separated sequencing products on the carrier.

19. The method as claimed in claim 16, further comprising, after step (f4), removing the hybridized at least one hybridization probe from the carrier, and thereafter repeating steps (f3) and (f4) using a different hybridization probe which comprises a DNA sequence which is complementary to a different single DNA fragment/adaptor complex.

20. A method for converting an already existing gene bank into a modified gene bank on which a simultaneous sequencing of nucleic acids can be carried out, wherein the already existing gene bank comprises a plurality of different DNA fragments which have been ligated into a base vector at an insertion region thereof, wherein the insertion region is flanked on a side by at least one restriction endonuclease recognition sequence which contains at least one of (1) a sequence of at least 7 nucleotides and (2) a 5'-CG-3' nucleotide sequence, the method comprising:

(a) cleaving the gene bank with an enzyme at the at least one restriction endonuclease recognition sequence to produce numerous DNA fragments;

(b) dividing the DNA fragments into several groups; and (c) ligating the divided DNA fragments from step (b) with a double-stranded DNA adaptor to produce ligation products, wherein the adaptor has a double-stranded region with a length of at least 5 nucleotides and ends on both sides which are suitable for ligation with the at least one restriction endonuclease recognition sequence, and wherein an adaptor having a different nucleotide sequence is ligated to a DNA fragment from each of the several groups.

21. The method as claimed in claim 20, further comprising, after step (c), (d) separating the ligation products from by-products.

22. The method as claimed in claim 20, wherein the double-stranded DNA adaptor has a sequence which is selected such that the at least one restriction endonuclease recognition sequence is eliminated by ligation of the double-stranded DNA adaptor in step (c).

23. The method as claimed in claim 21, wherein step (d) comprises recleaving the ligation products with the enzyme used in step (a).

24. The method as claimed in claim 20, wherein the at least one restriction endonuclease recognition sequence is selected from the group consisting of NotI, SfiI, RsrII, SgrAI, SwaI, PacI, AscI, PmeI, Sse83871, SrsI and IsceI.

25. The method as claimed in claim 20, wherein the adaptor molecule has a symmetrical sequence.

26. The method as claimed in claim 20, wherein the adaptor molecule has an unsymmetrical sequence.

27. The method as claimed in claim 20, wherein the insertion region is flanked on each side by different restriction endonuclease recognition sequences each containing at least one of (1) a sequence of at least 7 nucleotides and (2) a 5'-CG-3' nucleotide sequence, and wherein the steps (a)–(c) are carried out for each at least one restriction endonuclease recognition sequence.

* * * * *